United States Patent [19]

Zoechbauer et al.

[11] Patent Number: 4,999,013
[45] Date of Patent: Mar. 12, 1991

[54] CONTROLLABLE INTERFEROMETER

[75] Inventors: Michael Zoechbauer, Oberursel; Walter Fabinski, Kriftel, both of Fed. Rep. of Germany

[73] Assignee: Hartmann & Braun AG, Frankfurt, Fed. Rep. of Germany

[21] Appl. No.: 338,723

[22] Filed: Apr. 14, 1989

[30] Foreign Application Priority Data

Apr. 14, 1988 [DE] Fed. Rep. of Germany ....... 3812334

[51] Int. Cl.$^5$ ................................................ G01B 9/02
[52] U.S. Cl. ..................................... 356/346; 356/352
[58] Field of Search ........................ 356/346, 351, 352

[56] References Cited

U.S. PATENT DOCUMENTS

| 4,320,973 | 3/1982 | Fortunato et al. | 356/351 X |
| 4,595,292 | 6/1986 | Amodeo et al. | 356/352 X |
| 4,718,765 | 1/1988 | Fortunato et al. | 356/346 |
| 4,732,480 | 3/1988 | Fortunato et al. | 356/351 X |
| 4,735,506 | 4/1988 | Crane, Jr. et al. | 356/352 X |
| 4,743,114 | 5/1988 | Crane, Jr. | 356/352 X |

*Primary Examiner*—Davis L. Willis
*Assistant Examiner*—Matthew W. Koren
*Attorney, Agent, or Firm*—Ralf H. Siegemund

[57] ABSTRACT

Interferometric equipment for detecting a substance having a structure preferably a periodic or quasiperiodic absorption spectrum; the equipment includes a source of radiation, a path for that radiation that includes a sample cell with the substance to be detected, an interference filter and a detector, and is improved in that the interference filter is constructed as an electrically tunable filter, including a plate or cell element with semitransparent reflective boundaries serving as electrodes; an electrical voltage is applied to said electrodes such that the transmission characteristics of the filter is varied and the amplitude of the voltage as applied to these electrodes is an indication of that variation; and the thickness of the plate or cell is selected to meet one of the following criteria (i) a distance between the interference lines produced equals a distance of absorption lines within a periodic absorption spectrum of said substance; (ii) the equipment causes a line to be separated from the radiation having a bandwidth which is small as compared with a spacing between two absorption lines of the substance to be found (iii) the equipment causes a line to be separated from the radiation, to overlap an edge of an absorption band of the substance to be directed.

12 Claims, 2 Drawing Sheets

CONTROLLABLE INTERFEROMETER

BACKGROUND OF THE INVENTION

The present invention relates to interferometric equipment for detecting substances and more particularly the invention relates to interferometric equipment for detecting a substance under utilization of a structured, particularly a periodic or quasi-periodic absorption spectrum and using a source of radiation, a radiation path into which the substance to be investigated is placed, further using an interference filter having a thickness determined by the spacing of relevant interference line and further including a detector.

Interferometric equipment of the kind to which the invention pertains is for example shown German patent no. 26 04 471. The particular device here includes structure for the detection of a substance with a particular characterizable optical path difference and here on uses an assembly that includes the following elements and components: a polarizer, a double refracting plate or platelet having a thickness equal to the characteristic optical path length difference of the substance to be detected and further including a second polarizer operating as an analyzer. This device requires continuous rotation of the analyzer and, therefore, is generally subjected to mechanical wear. Moreover, this particular kind of motorically driven structure limits the application of the equipment and particularly reduces the lifetime as well as increases the extent of maintenance. This is often not desirable particularly in the case of monitoring and inspecting industrial processes.

An interferometric equipment operating with interference filters is also described by J.J. Howarth annd H.M. Stanier in "Journal of Scientific Instruments", 1965, volume 42, pages 526–528. Here an infrared process analyzer is used having a second interference filter of a higher order namely a Fabry-Perot filter in a definite manner that is attuned to a periodic absorption spectrum of the substance to be detected. One of the filters is a measuring filter and the other one is a reference filter. For time multiplexing acquisition of reference signals one uses a chopper wheel which again is a mechanically moving device so that this particular interferometric structure is again subject to wear and is limited in its application for reasons mentioned above.

DESCRIPTION OF THE INVENTION

It is an object of the present invention to provide a new and improved interferometric equipment for the detection of substances and more particularly is is an object of the present invention to improve structure for the detection of substance under utilization of a structured particularly a periodically or quasiperiodically structured absorption spectrum and which equipment that is to be improved includes a source of radiation, a holder for the substance, an interference filter and a detector.

It is another object of the present invention to provide a new and improved interferometric equipment making it possible to detect molecules in a highly selective manner under utilization of periodic or quasi-periodic absorption spectrum and particularly under avoidance of mechanically movable parts.

In accordance with the preferred embodiment of the present invention, the objects are attained in that it is suggested to provide an interference filter which is an electrically tunable filter, being comprised of a plate made of or a cell filled with an electro-optical material; the front sides of the plate or the cell is partially transparent-reflective; the transmission characteristics of the filter is shifted under utilization of an electrical voltage applied to the reflective front sides of the plate or cell whereby the amplitude of the signal is controlling as to the shift thus obtained. The thickness of the plate or cell is selected to meet one of the following criteria. (i) The distance of the resulting interference lines corresponds to the spacing of the absorption line of the substance to be detected; (ii) a line of the radiation can be separated from the spectrum having a bandwidth which is small in relation to the distance between two particular lines in relation to each other as far as the substance to be found is concerned; (iii) a line of the radiation that is being used will overlap with an edge of an absorption band of the substance to be detected.

The decisive element in this equipment is an interferometric element which is constructed as an electrically tunable filter made of electrooptical active material. If that material is a plate, certain crystal plates made of lithium niobate can be used with advantage. if the filter is a cell is should contain double refracting liquid crystals. Materials of this kind have an index of refraction which depends on any applied electrical field. The electrooptical plate or the liquid crystal cell is bounded optically by semitransparent and reflective front layers and so that in toto a Fabry-Perot interferometric element obtains. these layers serve also as electrodes. Through the degree of reflectivity as provided in this manner the half value width of the Fabry-Perot interferometric element can be adjacent in a manner that is known per se.

Depending on the kind of spectrum and the goal of the measurement such as high sensitivity, high selectivity or simple adaptability to the measuring task one can use a configuration in which relatively large portion of the absorption spectrum is covered through cascading of differently attuned filters of the kind suggested here generally. For high sensitivity it is particularly of advantage if a quasi-periodic line spectrum is present such as e.g. in the case of a CO molecule in the range of 4.6 micrometers. In this case one will choose the thickness of the electrooptical plate or the thickness of the liquid crystal cells such that the produced interferometric pattern of the characteristic optical wave difference is that of the molecules to be detected. This means there is a distance between the individual interference lines of the electrically tunable filter, to correspond exactly to the distance of the periodic absorption line of the particular material to be detected.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

FIG. 3b illustrates a modified measuring cell that can be used in the equipment of the kind shown in FIG. 3a.

Proceeding first to the description of FIGS. 3a and 3b various substances can be detected through employment of different plates or liquid crystal cells. FIG. 3a specifically shows the following components: a source of radiation L which issues and transmits a wide band radiation e.g. in the form of light. A particular optical filter F limits the radiation spectrum range to that part which is of interest i.e. may contain the frequencies covering the desired absorption lines of the substance to be detected. Within the radiation path the radiation is passed through a cuvette or sample, cell or the like, K, which includes or may include the substance to be detected or to be found.

Further downstream as far as the radiation flow is concerned in now provided the electrical tunable filter E which is the subject of the invention. In this specific case it includes a solid plate P made of an electrooptical material of a certain thickness and having its front faces covered by partially transparent, mirror surfaces S. These layers S provide in addition an electrofunction in that they are connected electrically to a modulation unit M which applies periodically variable or pulsating voltage to the two electrodes S.

A diaphragm B limits the interferometric range to the central part near the optical axis. In between the filter B and the diaphragm one may provide an objective lens O or the like which images or focuses the radiation into the focal point coinciding with a detector D. The radiation is converted into an electrical signal from which the requisite information can be obtained.

Figure 3A:
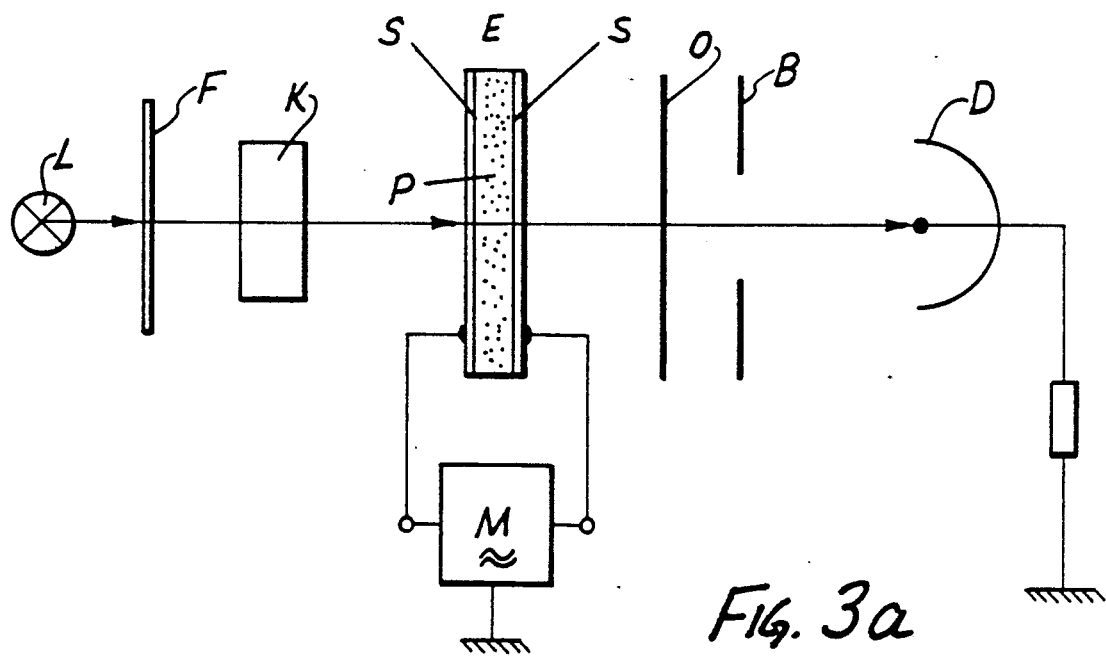
FIG. 3a illustrates somewhat schematically a preferred embodiment for practicing the best mode of the invention.
Figure 3B:
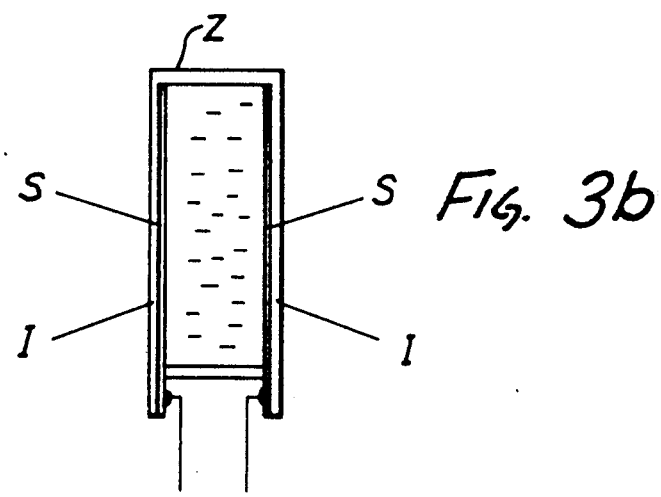
Figure 3C:
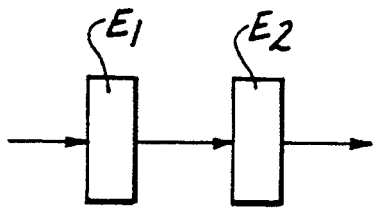
FIG. 3c shows a cascaded filter arrangement.

FIG. 3b illustrates a cell 2 filled with a liquid crystal. Reference character I denotes windows for radiation, and they carry the electrodes S. FIG. 3c shows that multiple filters, E1 and E2, can be cascaded to increase sensitivity and/or selectivity. The filters cover different absorption bands.

Figure 1:
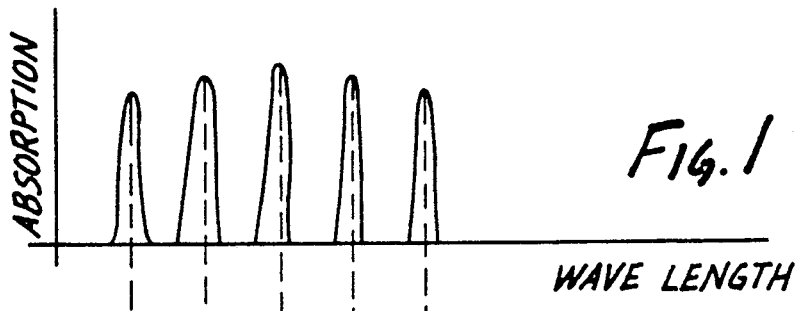
FIGS. 1, 2a and 2b illustrate certain diagrams relevant to the practice of the invention, when a periodic interference filter and line spectrum of the substance to be detected is used.
Figure 2A:
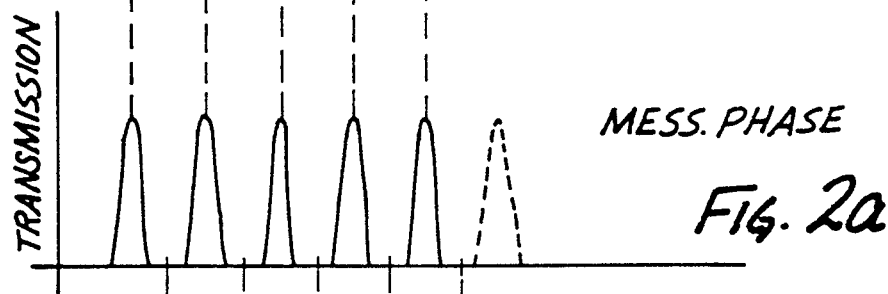

It is assumed that e.g. an interference pattern is used for the filter E which is represented in FIG. 2a. This interference pattern can be made to coincide and cover the periodic absorption line of a substance such as shown in FIG. 1. It is for this reason that the FIGS. 1 and 2a are shown in vertical alignment. The inventive equipment is assumed to be in a measuring phase characterized in maximum absorption as far as the substance to be found is concerned.

Figure 2B:
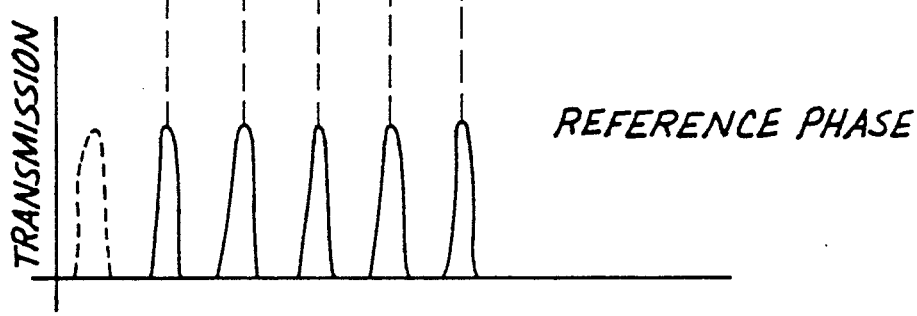

The absorption lines of the substance coincide with the transmission range pattern of the filter E so that the filter produces maximum dimming. As now an electric field is applied to the partially transparent mirror surfaces S of the electric tunable filter E one can in a simple fashion, namely through control of the voltage as applied, change the interferrence pattern. For instance, the interference pattern of the filter and the absorption line coincide as shown in FIG. 2a or the absorption lines just fall in between the interference line as shown in FIG. 2b. In this particular state also called the reference phase, absorption by the desired substance is essentially zero and dimming is minimized. Now through periodic modulation of the electrical field M one can change periodically from the measuring to the reference phase and vice versa and for this no movable parts are needed which is favorable when as compared with a mechanical modulation. The inventive electrical modulation permits also higher modulation frequency and that was found to improve the signal/noise ratio and also increases the speed of measurement acquisition. This situation and mode of operation is particularly advantageous for a high sensitivity.

High selectivity is particularly obtained if the inventive interferometer provides a single narrow line such that its bandwidth is small as compared with the distance between two lines within a periodic or quasiperiodic absorption spectrum of the substance. Now through simple shifting the central wavelength of this particular filter line and across the absorption lines of the substances one produces a useful signal whenever the measuring component is found to be within the absorption path. Since the correlation area to be covered is in this case smaller than in the first mentioned application with multiple lines and multiple absorption spectrum and interference pattern, one has to expect a larger noise level. On the other hand the advantage of this particular single line method is to be seen in the selection of the wavelength. One can shift it into a range wherein an overlap with any kind of interfering component is not present. This then provides a reduction in the noise level that is not available in the example mentioned above with reference to FIGS. 1 and 2.

A third possibility to employ the inventive equipment is to be seen when the spectrum is not a periodic one but at least has a certain structure. Through selection of the transmission wave length of the filter to be within a range of a relatively high gradient in the absorption as far as the measuring component is concerned, one detects its presence through a highly useful signal. The wavelength is selected so that the absorption of an interference component in this range is limited or is hardly dependent on the wavelength or not at all and now one obtains the desired selectivity in the same fashion.

The invention is not limited to the embodiments described above but all changes and modifications thereof, not constituting departures from the spirit and scope of the invention, are intended to be included.

We claim:

1. Interferometric equipment for detecting a substance having a structure yielding a periodic or quasiperiodic absorption spectrum, the equipment including a source of radiation, a path for that radiation that includes the substance to be detected, an interference filter and a detector, the improvement comprising:

the interference filter being constructed as an electrically tunable filter including a plate or cell element with semitransparent reflective boundaries serving as electrodes;

means for providing an electrical voltage to said electrodes such that the transmission characteristics of the filter is varied and the amplitude of the voltage as applied to these electrodes is an indication of that variation; and the thickness of the plate or cell providing for a distance between the interference lines as produced equaling a distance of absorption lines within a periodic absorption spectrum of said substance.

2. Interferometer as in Claim 1, said cell being a solid plate having front faces covered with electrodes.

3. Interferometer as in Claim 1, said filter being a cell filled with a double refracting liquid.

4. Interferometer as in Claim 1, there being plural differently attuned filters in said path.

5. Interferometric equipment for detecting a substance having a structure yielding a periodic or quasiperiodic absorption spectrum, the equipment including a source of radiation, a path for that radiation that includes the substance to be detected, an interference filter and a detector, the improvement comprising:

the interference filter being constructed as an electrically tunable filter including a plate or cell element with semitransparent reflective boundaries serving as electrodes;

means for providing an electrical voltage to said electrodes such that the transmission characteristics of the filter is varied and the amplitude of the voltage as applied to these electrodes is an indication of that variation; and the thickness of the plate or cell being such that the equipment by operation of the plate or cell causes a line to be separated from the radiation having a bandwidth which is small as compared with a spacing between two absorption lines of the substance to be found.

6. Interferometer as in Claim 5, said cell being a solid plate having front faces covered with electrodes.

7. Interferometer as in Claim 5, said filter being a cell filled with a double refracting liquid.

8. Interferometer as in Claim 5, there being plural differently attuned filters in said path.

9. Interferometric equipment for detecting a substance having a structure yielding a periodic or quasiperiodic absorption spectrum, the equipment including a source of radiation, a path for that radiation that includes the substance to be detected, an interference filter and a detector, the improvement comprising:

the interference filter being constructed as an electrically tunable filter including a plate or cell element with semitransparent reflective boundaries serving as electrodes;

means for providing an electrical voltage to said electrodes such that the transmission characteristics of the filter is varied and the amplitude of the voltage as applied to these electrodes is an indication of that variation; and such that the equipment by operation of the plate or cell causes a line to be separated from the radiation, to overlap an edge of the absorption band of the substance to be detected.

10. Interferometer as in Claim 9, said cell being a solid plate having front faces covered with electrodes.

11. Interferometer as in Clain 9, said filter being a cell filled with a double refracting liquid.

12. Interferometer as in Claim 9, there being plural differently attunded filters in said path.

* * * * *